United States Patent [19]

Ogura

[11] Patent Number: 5,680,869
[45] Date of Patent: Oct. 28, 1997

[54] BLOOD PRESSURE MEASURING APPARATUS

[75] Inventor: Toshihiko Ogura, Inuyama, Japan

[73] Assignee: Colin Corporation, Aichi-ken, Japan

[21] Appl. No.: 714,814

[22] Filed: Sep. 17, 1996

[30] Foreign Application Priority Data

Sep. 20, 1995 [JP] Japan ................... 7-241094

[51] Int. Cl.$^6$ ............................................. A61B 5/00
[52] U.S. Cl. .......................... 128/680; 128/681; 128/682
[58] Field of Search ......................... 128/672, 677, 128/680–7

[56] References Cited

U.S. PATENT DOCUMENTS

| | | |
|---|---|---|
| 4,228,506 | 10/1980 | Ripley et al. |
| 4,747,412 | 5/1988 | Yamaguchi ............... 128/680 |
| 4,944,305 | 7/1990 | Takatsu et al. ............ 128/680 |
| 4,967,756 | 11/1990 | Hewitt ...................... 128/680 |
| 4,995,399 | 2/1991 | Hayashi et al. ........... 128/680 |
| 5,337,750 | 8/1994 | Walloch ................... 128/680 |

FOREIGN PATENT DOCUMENTS

| | | |
|---|---|---|
| A-0 208 619 | 1/1987 | European Pat. Off. |
| A-2 679 675 | 1/1993 | France . |

Primary Examiner—Robert Nasser
Attorney, Agent, or Firm—Oliff & Berridge

[57] ABSTRACT

A blood pressure (BP) measuring apparatus including a first device for storing a set of BP data representing at least one BP value measured in a measuring operation, and a date and a time when the measuring operation is effected, thereby storing sets of BP data corresponding to measuring operations, a second device for storing a first one of the sets of BP data which belongs to a first number of sets of BP data which have early been stored by the first device, a third device for storing a second one of the sets of BP data which belongs to a second number of sets of BP data which have lately been stored by the first device, a fourth device for storing a third one of the sets of BP data which represents at least one BP value including a highest systolic BP value, a fifth device for storing a fourth one of the sets of BP data which represents at least one BP value including a lowest systolic BP value, and a recording device for recording (a) a graphic representation including first symbols each of which is indicative of the BP value represented by a corresponding one of the sets of BP data, in the order of the measuring operations, (b) a list containing the BP value, date, and time represented by each of the first to fourth sets of BP data, and (c) a second symbol in association with each of the four first symbols corresponding to the first to fourth sets of BP data, in the graphic representation.

17 Claims, 6 Drawing Sheets

BLOOD PRESSURE MEASURING APPARATUS

BACKGROUND OF THE INVENTION

1. Field of the Invention

The present invention relates to a blood pressure measuring apparatus which accumulatively stores measured blood pressure values and records, on a recording medium, a list showing each measured blood pressure value with the date and time when each value is obtained, and a graphic representation of a time-wise trend of the stored pressure pressure values.

2. Discussion of Related Art

There is known an automatic blood pressure (BP) measuring apparatus including a memory device such as a magnetic disc for storing measured BP values. Each time the BP measuring apparatus carries out a BP measurement on a living person, it records, on a recording sheet, a data list showing the prior BP values stored in the memory device, as well as the current BP value, together with the dates and times of measurement of those values. In addition, the measuring apparatus records, on the sheet, a graphic representation of a time-wise trend of the stored BP values, so that the person can read a time-wise change of the BP values. If the person compares the current BP value with the prior BP values in the graph, then he or she can judge whether the manner in which the current BP value is obtained is appropriate and/or whether his or her physical condition is normal. In addition, the person can read, on the data list, the BP value and the date and time which correspond to a significant change in the graph.

In the above BP measuring apparatus, however, all measured BP values are stored in the memory device. Accordingly, if the number of stored BP values increases, the data list becomes so large that it needs a long time to specify a particular BP value on the list and that the amount of consumption of the recording sheet increases. In addition, since BP measurements are not periodically carried out on a person, respective symbols corresponding to the BP measurements are not uniformly plotted along a time axis in the graph.

SUMMARY OF THE INVENTION

It is therefore an object of the present invention to provide a blood pressure measuring apparatus which records, on a recording medium, a graphic representation of a time-wise trend of stored blood pressure values and a list showing particular ones selected from the stored blood pressure values and which largely reduces the amount of consumption of the recording medium.

The above object may be achieved according to the present invention, which provides an apparatus for measuring a blood pressure value of a living subject, comprising a blood pressure measuring device which measures, in each of a plurality of measuring operations, at least one blood pressure value of the subject including a systolic blood pressure value of the subject, a first storing device which stores a set of blood pressure data which represents the at least one blood pressure value measured in the each measuring operation of the blood pressure measuring device, and a date and a time when the each measuring operation is carried out by the blood pressure measuring device, so that the first storing device stores a plurality of sets of blood pressure data corresponding to the plurality of measuring operations, a second storing device which stores a first one of the sets of blood pressure data which belongs to a first number of sets of blood pressure data which have early been stored by the first storing device, a third storing device which stores a second one of the sets of blood pressure data which belongs to a second number of sets of blood pressure data which have lately been stored by the first storing device, a fourth storing device which stores a third one of the sets of blood pressure data which represents at least one blood pressure value including a highest systolic blood pressure value of the respective systolic blood pressure values represented by the sets of blood pressure data except the first and second sets of blood pressure data, a fifth storing device which stores a fourth one of the sets of blood pressure data which represents at least one blood pressure value including a lowest systolic blood pressure value of the respective systolic blood pressure values represented by the sets of blood pressure data except the first and second sets of blood pressure data, and a recording device which records, on a recording medium, (a) a graphic representation comprising a plurality of first symbols each of which is indicative of the at least one blood pressure value represented by a corresponding one of the sets of blood pressure data, in an order of the measuring operations, (b) a list containing the at least one blood pressure value, date, and time represented by each of the first, second, third, and fourth sets of blood pressure data, and (c) a second symbol in association with each of the four first symbols corresponding to the first, second, third, and fourth sets of blood pressure data, in the graphic representation.

In the blood pressure (BP) measuring apparatus constructed as described above, the BP values indicated in the list are limited to only those represented by the four sets of BP data that are particularly important of all the stored sets of BP data indicated in the graphic representation. Thus, the amount of consumption of the recording medium is largely reduced. In addition, in the graphic representation, the second symbols are recorded in association with the four first symbols corresponding to the four sets of BP data, so that the BP values indicated in the list can easily be associated with the corresponding first symbols in the graphic representation. Since the four sets of BP data representing the BP values indicated in the list include the early and lately stored sets of BP data, the subject can easily and quickly see how long the BP measurements have been carried out on him or her.

According to a preferred feature of the present invention, the recording device comprises means for recording, on the recording medium, the graphic representation such that the first symbols are plotted at a regular interval of distance along an axis indicative of the order of the measuring operations. In this case, the subject can easily read a time-wise change of the BP values from the graphic representation. The axis along which the first symbols are plotted may extend parallel to the direction of width of the recording medium, such as a web or roll of recording sheet. In the last case, even if the number of first symbols increases in the graph as the number of BP measurements increases, the amount of consumption of the recording sheet does not increase.

According to another feature of the present invention, the second storing device comprises means for storing, as the first set of blood pressure data, one of the sets of blood pressure data which represents the oldest date and time of the respective dates and times represented by the sets of blood pressure data.

According to another feature of the present invention, the third storing device comprises means for storing, as the second set of blood pressure data, one of the sets of blood pressure data which represents the second latest date and time of the respective dates and times represented by the sets of blood pressure data.

According to another feature of the present invention, the BP measuring apparatus further comprises a sixth storing device which stores a set of temporary blood pressure data which represents, as at least one temporary blood pressure value, at least one blood pressure value measured by the blood pressure measuring device in each of a plurality of measuring operations within a predetermined time duration, thereby storing a plurality of sets of temporary blood pressure data corresponding to the plurality of measuring operations within the time duration, and the first storing device comprises means for selecting one of the sets of temporary blood pressure data which represents at least one temporary blood pressure value including a lowest temporary systolic blood pressure value of the respective temporary systolic blood pressure values represented by the sets of temporary blood pressure data, and storing the selected one set of temporary blood pressure data as a set of proper blood pressure data representing at least one proper blood pressure value obtained within the time duration, the at least one proper blood pressure value including the lowest temporary systolic blood pressure value as a proper systolic blood pressure value.

According to another feature of the present invention, the BP measuring apparatus further comprises a card reader which reads identification data recorded on a data card which is inserted in the card reader by the subject.

According to another feature of the present invention, the first storing device comprises means for storing the sets of blood pressure data on the data card being inserted in the card reader.

According to another feature of the present invention, the BP measuring apparatus further comprises a a registering device which registers identification data identical With the identification data recorded on the data card, and judging means for judging whether the identification data read by the card reader from the data card inserted by the subject are identical with the identification data registered by the registering device.

According to another feature of the present invention, the first storing device comprises means for accumulatively storing the sets of blood pressure data in association with the registered identification data.

According to another feature of the present invention, the blood pressure measuring device comprises means for measuring, in the each measuring operation, at least a systolic and a diastolic blood pressure value of the subject.

According to another feature of the present invention, the blood pressure measuring device comprises an inflatable cuff which is adapted to be wound around a body portion of the subject.

According to another feature of the present invention, the second storing device comprises means for selecting the first set of blood pressure data from the sets of blood pressure data stored by the first storing device, and a memory which stores the selected first set of blood pressure data.

According to another feature of the present invention, the third storing device comprises means for selecting the second set of blood pressure data from the sets of blood pressure data stored by the first storing device, and a memory which stores the selected second set of blood pressure data.

According to another feature of the present invention, the fourth storing device comprises means for selecting the third set of blood pressure data from the sets of blood pressure data stored by the first storing device, and a memory which stores the selected third set of blood pressure data.

According to another feature of the present invention, the fifth storing device comprises means for selecting the fourth set of blood pressure data from the sets of blood pressure data stored by the first storing device, and a memory which stores the selected fourth set of blood pressure data.

According to another feature of the present invention, the BP measuring apparatus further comprises a pulse-rate measuring device which measures a pulse-rate value of the subject in the each measuring operation of the blood pressure measuring device, and wherein the first storing device stores the set of blood pressure data representing the pulse-rate value measured by the pulse-rate measuring device in the each measuring operation of the blood pressure measuring device.

According to another feature of the present invention, the first storing device comprises a memory which accumulatively stores the sets of blood pressure data.

BRIEF DESCRIPTION OF THE DRAWINGS

The above and optional objects, features, and advantages of the present invention will better be understood by reading the following detailed description of the preferred embodiments of the invention when considered in connection with the accompanying drawings, in which.

DETAILED DESCRIPTION OF THE PREFERRED EMBODIMENTS

Referring to FIGS. 1 to 6, there will described an automatic blood pressure (BP) measuring apparatus 10 to which the present invention is applied.

Figure 1:
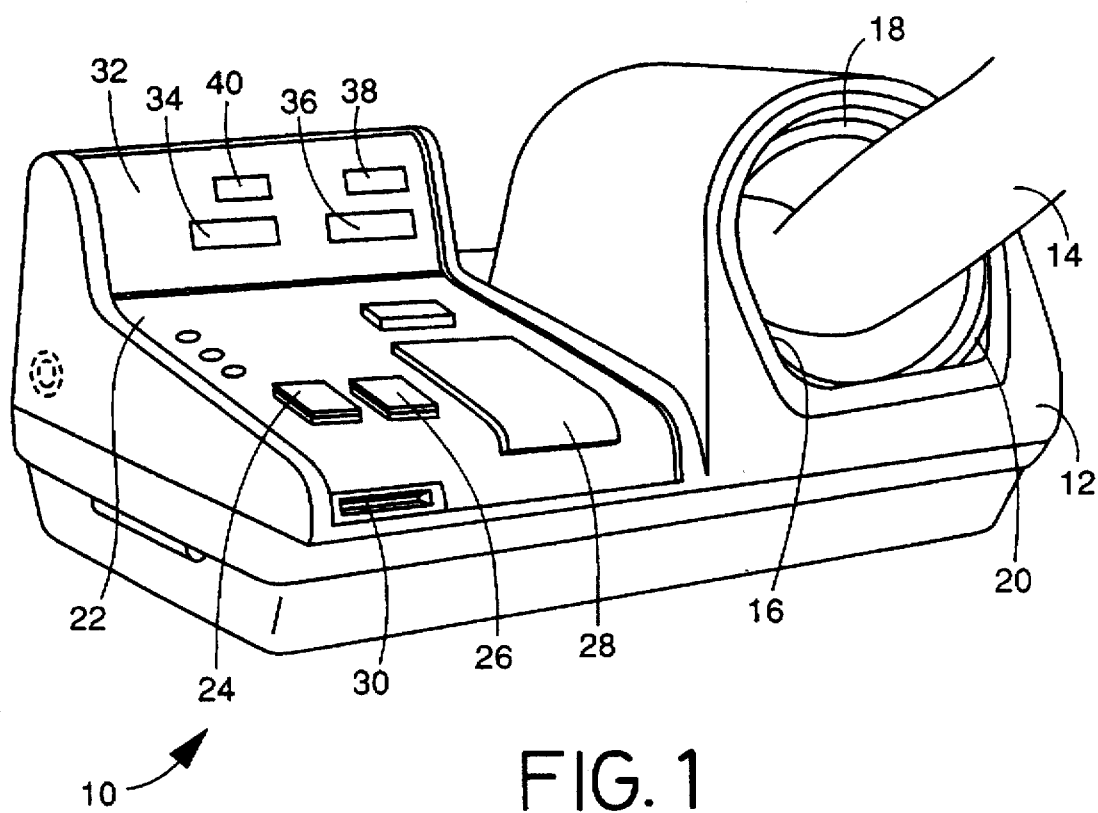
FIG. 1 is a perspective view of a blood pressure (BP) measuring apparatus as one embodiment of the present invention.

In FIG. 1, reference numeral 12 designates a housing of the BP measuring apparatus 10. The BP measuring apparatus 10 includes a tunnel-like, cylindrical hollow portion which provides an arm receiver 16 into which an arm 14 of a living subject is inserted for measurement of his or her BP value. Inside the arm receiver 16, an elongate belt 20 is supported such that the belt 20 takes a generally cylindrical shape. An inflatable cuff 18 which is provided by a flexible cloth bag and a rubber bag accommodated in the cloth bag, is secured to the inner surface of the elongate belt 20.

The BP measuring apparatus 10 has an operation panel 22 including a START switch 24, a STOP switch 26, a printer 28, and a card insertion slot 30. The BP measuring apparatus 10 further has a display panel 32 including a SAP display 34, a DAP display 36, a PR display 38, and a date and time display 40. The abbreviations "SAP", "DAP", and "PR" represent a systolic BP value, a diastolic BP value, and a pulse rate, respectively.

Figure 2:
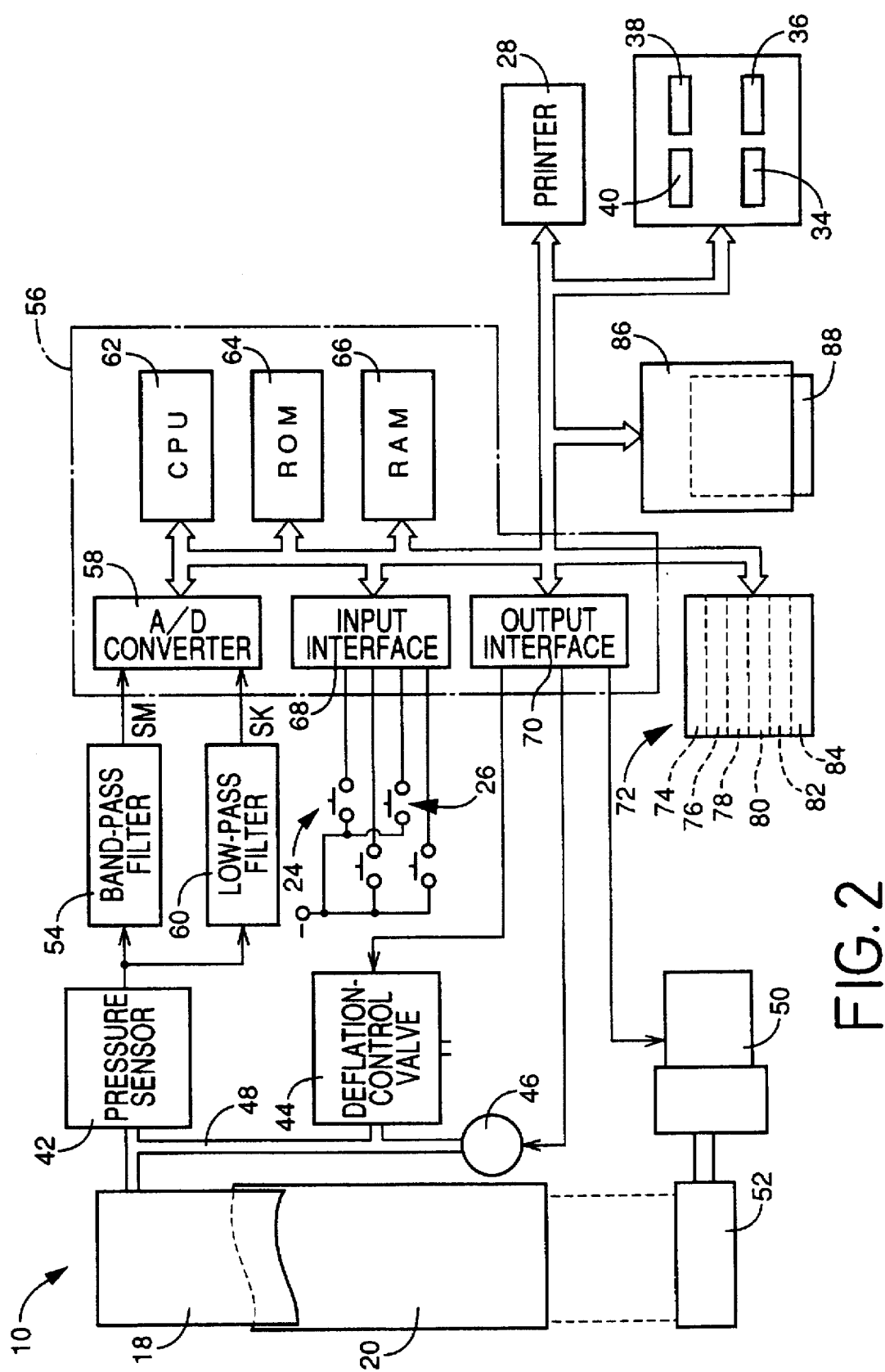
FIG. 2 is a block diagram showing the construction of the apparatus of FIG. 1.

FIG. 2 shows the construction of the BP measuring apparatus 10. In the figure, the inflatable cuff 18 is connected via piping 48 to a pressure sensor 42, a deflation-control valve 44, and an air pump 46. The pressure sensor 42 detects an air pressure in the cuff 18 and outputs an electric signal representing the detected cuff pressure. The elongate belt 20 which takes a cylindrical shape in the arm receiver 16 and to which the inflatable cuff 18 is secured, is fixed at one of longitudinal ends thereof to the housing 12 and is connected at the other longitudinal end to a rotatable drum 52 which is driven or rotated by a direct-current (DC) motor 50 via reduction gears. The elongate belt 20 or the inflatable cuff 18 is tightened, and loosened, by the DC motor 50.

The output signal of the pressure sensor 42 is supplied to a band-pass filter 54, which extracts, from the received signal, an alternating-current (AC) component representing a pulse wave, i.e., pressure oscillation propagated from the subject to the cuff 18 and supplies the extracted AC component as a pulse-wave signal, SM, to an analog to digital (A/D) converter 58 of an electronic control circuit 56. The pulse wave represented by the pulse-wave signal SM is produced from the brachial artery of subject's arm 14 being pressed under the cuff 18, and is propagated to the cuff 18. The output signal of the pressure sensor 42 is also supplied to a low-pass filter 60, which extracts, from the received signal, a direct-current (DC) component representing a static pressure in the cuff 18 and supplies the extracted DC component as a cuff-pressure signal, SK, to the A/D converter 58 of the control circuit 56. The static cuff pressure represented by the cuff-pressure signal SK changes when the cuff 18 is tightened or loosened by the DC motor 50.

The electronic control circuit 56 is provided by a microcomputer including a central processing unit (CPU) 62, a read only memory (ROM) 64, a random access memory (RAM) 66, an input interface circuit 68, and an output interface circuit 70. The CPU 62 processes input signals according to the control programs pre-stored in the ROM 64 by utilizing the temporary-storage function of the RAM 66, outputs a drive signal to the printer 28, and outputs display signals to the displays 34-40. When a BP measurement is carried out, the CPU 62 supplies a drive signal to the DC motor 50 to wind the cuff 18 around the upper arm 14 of the subject being inserted in the arm receiver 16, subsequently supplies a drive signal to the air pump 46 to inflate the cuff 18 and thereby press the upper arm 14, and then supplies a drive signal to the deflation-control valve 44 to reduce gradually or slowly the pressure of the cuff 18, so that the CPU 62 obtains the pulse-wave signal SM and the cuff-pressure signal SK from the pressure sensor 42 via the respective filters 54, 60 during this cuff-pressure reducing operation, determines a systolic and a diastolic BP values SAP, DAP of the subject in a known oscillometric BP measuring method based on the obtained signals SM, SK, and supplies display signals to the SAP and DAP displays 34, 36 to display the determined BP values SAP, DAP, respectively.

In addition, the CPU 62 produces a set of temporary BP data which represents the thus determined BP values SAP, DAP as temporary BP values, and represents a date and a time when the BP values are obtained, and stores the set of temporary BP data in a temporary BP data memory area 74 of a BP-data storing device 72. The CPU 62 accumulatively stores a plurality of sets of temporary BP data produced in a plurality of BP measurements carried out within five minutes after the first one of BP measurements is started on the BP measuring apparatus 10. The CPU 62 selects, from all the sets of temporary BP data accumulatively stored in the temporary BP data memory area 74 within the five minutes, one set of temporary BP data which represents the lowest systolic BP value SAP of the respective systolic BP values SAP represented by all the stored sets of temporary BP data, and stores the selected set of temporary BP data, as a set of proper BP data representing proper systolic and diastolic BP values, in a proper BP data memory area 76 of the BP-data storing device 72.

Furthermore, the CPU 62 selects, from all the sets of proper BP data accumulatively stored in the proper BP data memory area 76, one set of proper BP data representing the oldest date and time, and stores the selected set of proper BP data in an early BP data memory area 78 of the BP-data storing device 78; the CPU 62 selects, from all the sets of proper BP data stored in the proper BP data memory area 76, one set of proper BP data representing the second latest date and time, and stores the selected set of proper BP data in a late BP data memory area 80 of the storing device 72; the CPU 62 selects, from all the sets of proper BP data stored in the proper BP data memory area 76, one set of proper BP data representing the highest systolic BP value SAP of the respective systolic BP values SAP represented by all the stored sets of proper BP data (except the two sets of proper BP data stored in the early and late BP data memory areas 78, 80, respectively), and stores the selected set of proper BP data in a highest-SAP BP data memory area 82 of the storing device 72; and the CPU 62 selects, from all the sets of proper BP data stored in the proper BP data memory area 76, one set of proper BP data representing the lowest systolic BP value SAP of the respective systolic BP values SAP represented by all the stored sets of proper BP data (except the two sets of proper BP data stored in the early and late BP data memory areas 78, 80, respectively), and stores the selected set of proper BP data in a lowest-SAP BP data memory area 84 of the storing device 72. The BP-data storing device 72 is provided by a well-known memory device such as a magnetic disk, a magnetic tape, a volatile semiconductor memory, or a non-volatile semiconductor memory.

Hereinafter, there will be described the operation of the automatic BP measuring apparatus 10 constructed as described above, by reference to the flow charts of FIGS. 3, 4, and 5.

Figure 3:
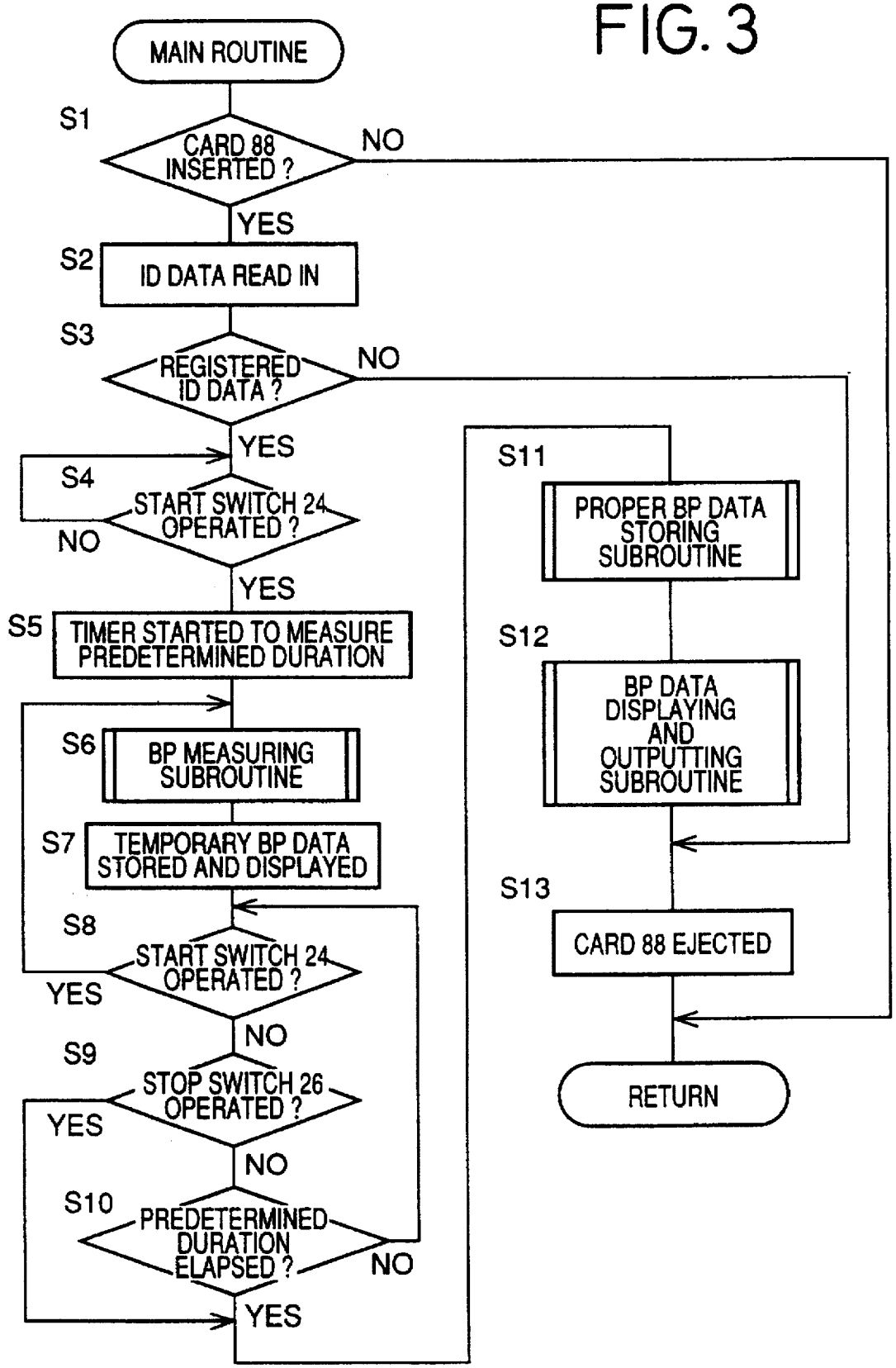
FIG. 3 is a flow chart representing a control program according to which the apparatus of FIG. 1 is operated.

First, at Step S1 of FIG. 3, the CPU 62 judges whether a magnetic card 88 has been inserted in a card reader 86 through the insertion slot 30 by a living person. If a negative judgment is made at Step S1, the current cycle of the main routine is ended. On the other hand, if a positive judgment is made at Step S1, the control of the CPU 62 goes to Step S2 to read identification (ID) data which are magnetically recorded on the magnetic card 88 and which identify the person who carries the card 88.

Step S2 is followed by Step S3 to judge whether the ID data read from the magnetic card 88 are identical with ID data registered in an appropriate memory area of the BP-data storing device 72. If a negative judgment is made at Step S3, the control of the CPU 62 goes to Step S13 to eject the magnetic card 88 from the card reader 86 through the slot 30. On the other hand, if a positive judgment is made at Step S3, i.e., the ID data read from the magnetic card 88 are identical with registered ID data, the control of the CPU 62 goes to Step S4 to judge whether the START switch 24 has been operated to start a blood pressure (BP) measurement.

If the judgment made at Step S4 is negative, Step S4 is repeated until a positive judgment is made. Meanwhile, if a positive judgment is made at Step S4, the control of the CPU 62 goes to Step S5 to start a timer to measure a predetermined time duration, i.e., 5 minutes during which a plurality of BP measurements may be carried out on the person. Step S5 is followed by Step S6 to effect a BP measuring subroutine in which a systolic, a diastolic, and a mean BP value SAP, DAP, MAP, and a pulse-rate value PR, of the person are measured. This measurement is the first measurement within the five minutes after the timer is started at Step S5. More specifically described, the pressure of the cuff 18 is automatically increased according to a predetermined procedure, and the BP values SAP, DAP, MAP of the person are determined based on the signals SM, SK obtained during the slow decreasing of the cuff pressure, in the known oscillometric BP measuring method. The systolic and diastolic BP values SAP, DAP are determined based on the variation of respective magnitudes of heartbeat-synchronous pulses of the pulse-wave signal SM obtained during the slow cuff-pressure decreasing. The mean BP value MAP is determined as being equal to the cuff pressure at the time of occurrence or detection of a heartbeat-synchronous pulse having the greatest or maximum amplitude. The pulse-rate value PR is determined from the time interval between the respective times of detection of two successive heartbeat-synchronous pulses of the pulse-wave signal SM which is the same as used to determine the BP values SAP, DAP, MAP.

Step S6 is followed by Step S7 to store a set of temporary BP-PR data which represents the BP and pulse-rate values SAP, DAP, MAP, PR determined at Step S6, as temporary BP and pulse rate values, and represents the date and time of measurement of those values, in the temporary BP data memory area 74 of the BP-data storing device 72. Further, at Step S7, the determined BP and pulse-rate values SAP, DAP, PR are displayed on the SAP, PAP, and PR displays 34, 36, 38, respectively.

Step S7 is followed by Step S8 to judge whether the START switch 24 has been operated again to start another BP measurement. If a positive judgment is made at Step S8, Steps S6 and S7 are repeated. In this case, data indicative of the values SAP, DAP, MAP, PR obtained at Step S6 in the second measurement are stored, as another set of temporary BP data, in the temporary BP data memory area 74 of the BP-data storing device 72. On the other hand, if a negative judgment is made at Step S8, that is, if the START switch 24 has not been operated, the control of the CPU 62 goes to Step S9 to judge whether the STOP switch 26 has been operated not to carry out any more BP measurement. If a positive judgment is made at Step S9, no additional measurement is carried out. Accordingly, even if the predetermined time duration (i.e., 5 minutes) may not have elapsed yet, the control of the CPU 62 goes to Step S11. On the other hand, if a negative judgment is made at Step S9, the control goes to Step S10 to judge whether the timer which had been started at Step S5 has measured the predetermined time duration, i.e., 5 minutes. If a negative judgment is made at Step S9, it means that another BP measurement may be ordered by the person. In this case, Step S8 and the following steps are repeatedly executed. Meanwhile, if a positive judgment is made at Step S10, namely, if the timer has measured the 5 minutes, Step S10 is followed by Step S11 to effect a proper BP data storing subroutine.

Figure 4:
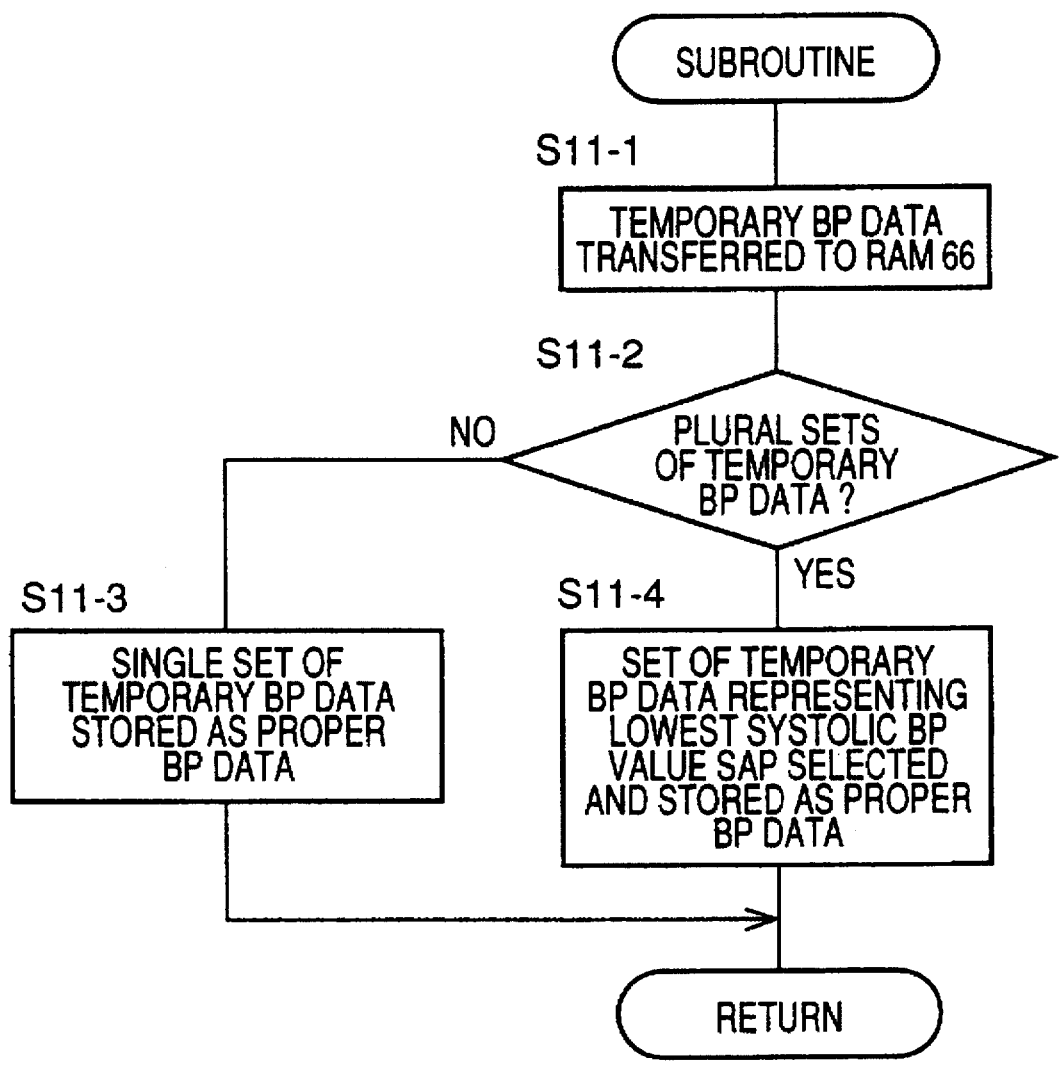
FIG. 4 is a flow chart representing a subroutine effected at Step S11 of the flow chart of FIG. 3.

The proper BP data storing subroutine of Step S11 is represented by the flow chart of FIG. 4. This subroutine starts with Step S11-1 to transfer the set or sets of temporary BP data stored in the temporary BP data memory area 74 of the BP-data storing device 72, to the RAM 66. Step S11-1 is followed by Step S11-2 to judge whether a plurality of BP measurements have been effected within the predetermined time, namely, a plurality of sets of temporary BP data have been stored in the temporary BP data memory area 74 as a result of execution of a plurality of cycles of the BP measuring subroutine of Step S6. If a negative judgment is made at Step S11-2, it means that only one BP measurement has been effected, and the control of the CPU 62 goes to Step S11-3 to store the single set of temporary BP data as a set of proper BP data, in the proper BP data memory area 76. That is, data indicative of the measured values SAP, DAP, MAP, PR are stored in the proper BP data memory area 76, together with data indicative of the date and time of measurement of those values. On the other hand, if a positive judgment is made at Step S11-2, it means that a plurality of BP measurements have been effected, and the control of the CPU 62 goes to step S11-4 to select the most appropriate set of temporary BP data from the stored sets of temporary BP data, and store the selected set of temporary BP data as a set of proper BP data in the proper BP data memory area 76. More specifically described, at Step S11-4, one of the stored sets of temporary BP data which represents the lowest systolic BP value SAP is stored as the set of proper BP data in the proper BP data memory area 76. The set of proper BP data which represents the values SAP, DAP, MAP, PR as proper values are stored in the proper BP data memory area 76, together with data indicative of the date and time when the predetermined time (i.e., five minutes) has elapsed. At each of Steps S11-3 and S11-4, the set of proper BP data is stored in association with the registered ID data identifying the person.

Figure 5:
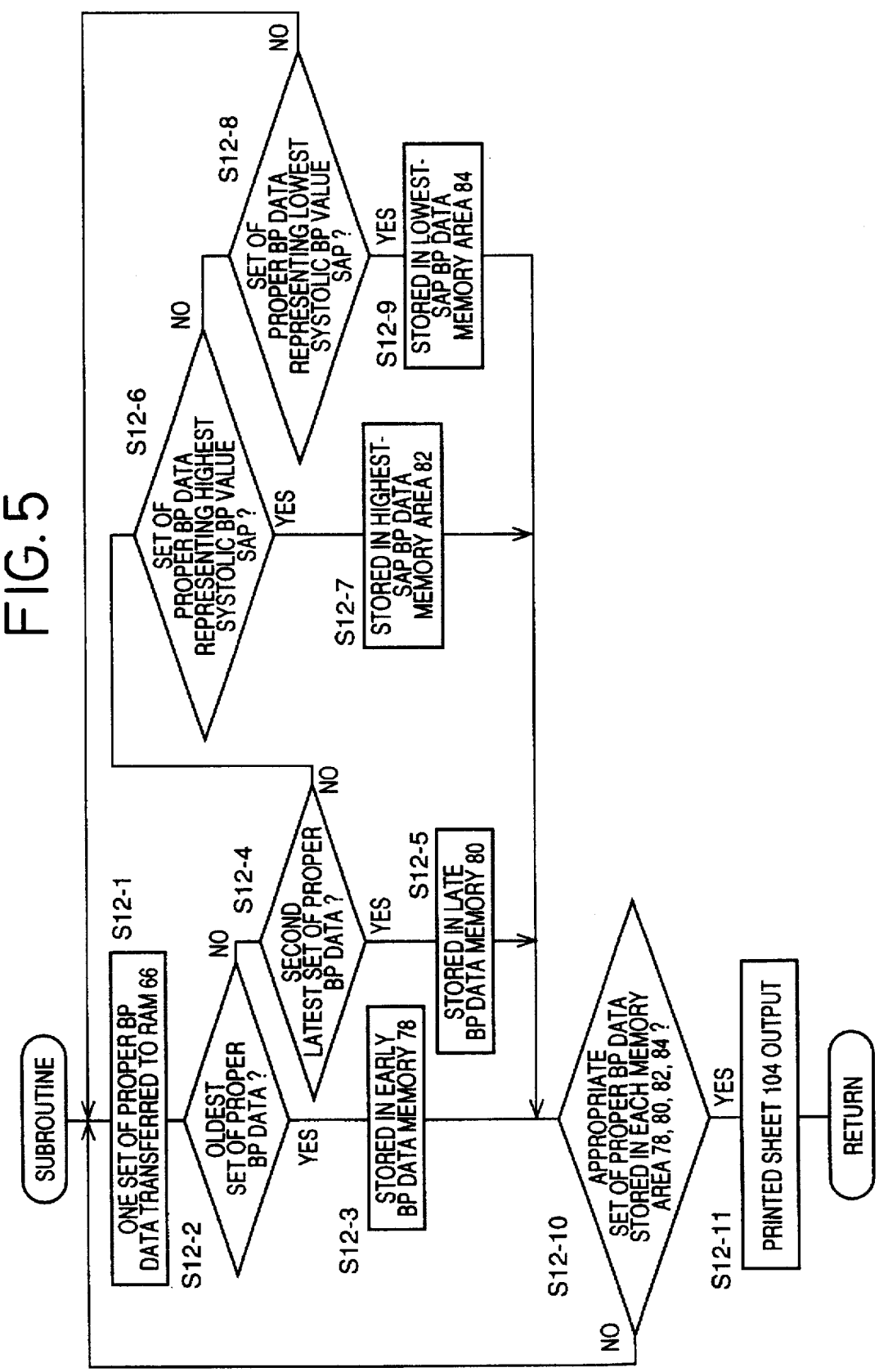
FIG. 5 is a flow chart representing a subroutine effected at Step S12 of the flow chart of FIG. 3.

The proper BP data storing subroutine of Step S11 is followed by Step S12 to effect a displaying and outputting subroutine represented by the flow chart of FIG. 5. The subroutine of FIG. 5 starts with Step S12-1 to transfer, to the RAM 66, each one of the set or sets of proper BP data which have accumulatively been stored in the proper BP data memory area 76 in association with the ID data of the person, in the order of storing of the sets of proper BP data in the proper BP data memory area 76. Subsequently, the control of the CPU 62 goes to Step S12-2 to judge whether the one set of proper BP data transferred to the RAM 66 at Step S12-1 represents the oldest date and time. If the judgment at Step S12-2 is positive, Step S12-2 is followed by Step S12-3 to store the set of proper BP data indicative of the values SAP, DAP, MAP, PR, in the early BP data memory area 78, together with the data indicative of the date and time of measurement of those values.

If a negative judgment is made at Step S12-2, the control of the CPU 62 goes to Step S12-4 to judge whether the one set of proper BP data stored in the RAM 66 at Step S12-1 represents the second latest date and time. If a positive judgment is made at Step S12-4, the control of the CPU 62 goes to Step S12-5 to store, in the late BP data memory area 80, the set of proper BP data indicative of the values SAP, DAP, MAP, PR together with the data indicative of the date and time of measurement of those values.

If a negative judgment is made at Step S12-4, Step S12-6 is implemented to judge whether the systolic BP value SAP represented by the one set of proper BP data stored in the RAM 66 at Step S12-1 is the highest of the respective values SAP represented by the sets of proper BP data stored in the proper BP data memory area 76, except for the sets of proper BP data stored in the memory areas 78, 80. If a positive decision is made at Step S12-6, the control goes to Step S12-7 to store the set of proper BP data indicative of the values SAP, DAP, MAP, PR in the highest-SAP BP data memory area 82, together with the data indicative of the date and time of measurement of those values.

If a negative judgment is made at Step S12-6, the control of the CPU 62 goes to Step S12-8 to judge whether the systolic BP value SAP represented by the one set of proper BP data stored in the RAM 66 at Step S12-1 is the lowest, except for the sets of proper BP data stored in the memory areas 78, 80. If a positive judgment is made at Step S12-8, Step S12-9 is implemented to store the set of proper BP data indicative of the values SAP, DAP, MAP, PR in the lowest-SAP BP data memory area 84, together with the data indicative of the date and time of measurement of those values.

If a negative judgment is made at Step S12-8, the control of the CPU 62 goes back to Step S12-1 to transfer the next set of proper BP data stored in the proper BP data memory area 76, to the RAM 66, and effects the following steps with respect to the next set of proper BP data stored in the RAM 66. Step S12-3, S12-5, S12-7, or S12-9 is followed by Step S12-10 to judge whether an appropriate set of proper BP data has been stored in each of the respective memory areas 78, 80, 82, 84. If a negative judgment is made at Step S12-10, the control of the CPU 62 goes back to Step S12-1 and the following steps. On the other hand, if a positive judgment is made at Step S12-10, the control goes to Step S12-11.

Figure 6:
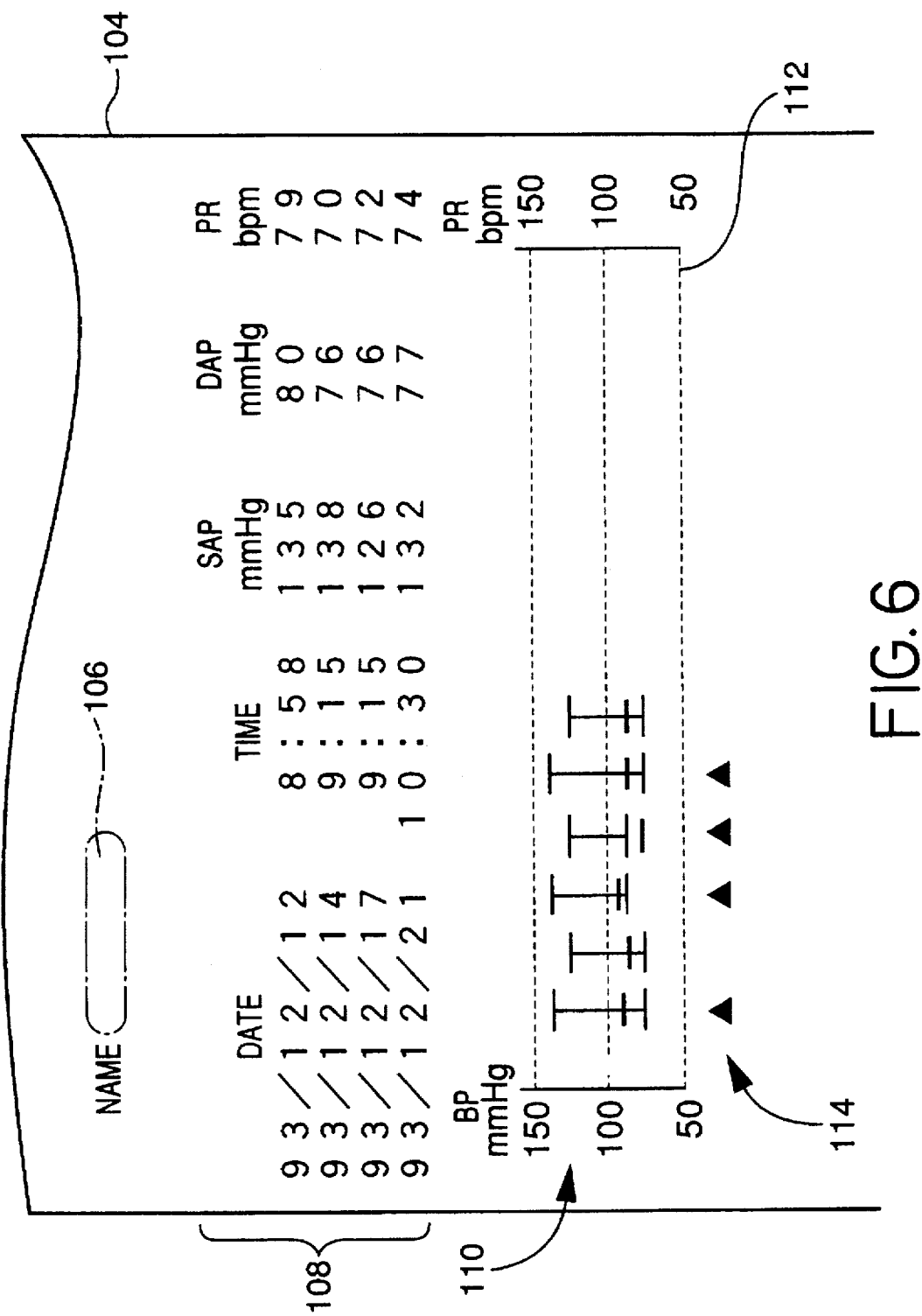
FIG. 6 is a view showing a printed sheet which is output from the apparatus of FIG. 1 as a result of operation thereof according to the flow chart of FIG. 3.

At Step S12-11, the CPU 62 commands the printer 28 to output or record, on a recording sheet 104, the BP data stored in the BP-data storing device 72, as shown in FIG. 6. More specifically described, in an upper, left-hand portion of the sheet 104, the printer 28 records a name 106 of the person identified by the ID data or magnetic card 88. The name 106 of the person is represented by the registered ID data identifying the person. Bellow the name 106, the printer 28 records (a) a data list 108 showing the date and time of measurement and the measured BP and pulse-rate values represented by each of the four sets of BP and pulse-rate data respectively stored in the early BP data memory area 78, late BP data memory area 80, highest-SAP BP data memory area 82, and lowest-SAP BP data memory area 84; and (b) a graphic representation 110 of all the sets of proper BP data accumulatively stored in the proper BP data memory area 76. The graphic representation 110 shows, along a common axis of abscissa 112 indicative of time, a series of vertical bars each of which has a top and a bottom thin horizontal segment which represent a systolic and a diastolic BP value SAP, DAP, respectively, and has a thick horizontal segment which represents a pulse-rate value PR, in the order of measurement. The bars are plotted at a regular interval of distance along the time axis 112. A symbol, ▲ 114, is recorded in association with each of the four bars, shown in the graphic representation 110, which respectively correspond to the four sets of proper BP data listed in the data list 108. Step S12 is followed by Step S13 of the main routine of FIG. 3 to eject the magnetic card 88 from the card reader 86.

As is apparent from the foregoing description, in the present embodiment, the data list 108 printed on the recording sheet 104 shows only the BP values, pulse-rate value, date, and time represented by each of the four sets of proper BP data stored in the four memory areas 78, 80, 82, 84. The four sets of proper BP data respectively stored in the four memory areas 78–84 are very important data. In addition, in the graphical representation 110, the symbol 114 is recorded in association with each of the four vertical bars corresponding to the four sets of proper BP data stored in the four memory areas 78–84. Thus, the person who carries the card 88 can easily find out, on the sheet 104, the BP values, pulse-rate value, date, and time represented by each of the four sets of proper BP data stored in the four memory areas 78–84. In addition, the amount of consumption of the sheet 104 can be reduced. Moreover, since the list 108 shows the oldest BP values and the second latest BP values, the person can easily and quickly understand the time span during which the BP values represented by the graph 110 have been obtained. Furthermore, since the graph 110 shows the respective measured BP values represented by all the sets of proper BP data, in the order of measurement, such that the vertical bars are plotted at a regular interval of distance along the time axis 112, the person can easily understand the time-wise change of his or her BP values. Since the time axis 112 has a predetermined length shorter than the width of the recording web 104, the amount of consumption of the web 104 does not increase even though the number of bars may increase along the axis 112 in the graph 110. The web 104 is accommodated in the form of a roll in the housing 12 of the BP measuring apparatus 10.

While the present invention has been described in its preferred embodiment, the present invention may otherwise be embodied.

For example, in the illustrated embodiment, Steps S5 and S7-11 may be omitted. In the latter case, when the systolic and diastolic BP values and the pulse-rate value are measured at Step S6, those values are displayed on the displays 34, 36, 38, respectively, and a set of BP data representing those values is stored in the memory area 76. Then, the control of the CPU 62 goes to Step S12.

In the illustrated embodiment, the CPU 62 determines the BP values of the living person according to the known oscillometric BP measuring method, in the BP measuring subroutine of Step S6 of FIG. 3. However, the BP measuring apparatus 10 may be modified to measure BP values according to a known Korotkoff-sound BP measuring method in which one or more BP values are determined based on detected Korotkoff sounds. In the latter case, the BP measuring apparatus 10 needs a microphone which detects Korotkoff sounds which are produced from arteries of a body portion (e.g., upper arm 14) of a living person while the pressure of the cuff 18 pressing the upper arm 14 is changed, i.e., gradually decreased or increased.

In the illustrated embodiment, the sets of proper BP data are accumulatively stored in the BP-data storing device 72. However, the sets of proper BP data may accumulatively be stored on the magnetic card 88, that is, another proper BP data memory area may be provided on the magnetic card 88. In the latter case, the various memory areas 74–84 may be provided in the RAM 66, and each set of proper BP data may be transferred from the proper BP data memory area 76 of the RAM 66 to that provided on the magnetic card 88, before the card 88 is ejected from the card reader 86. In this case, the BP-data storing device 72 may be replaced by the RAM 66.

Although in the illustrated embodiment the early BP data memory area 78 stores the oldest set of proper BP data and the late BP data memory area 80 stores the second latest set of proper BP, it is possible that the early BP data memory area 78 may store a set of proper BP data belonging to a predetermined number of sets of proper BP data which have early been stored in the memory area 76 and that the late BP data memory area 80 may store a set of proper BP belonging to a predetermined number of sets of proper BP data which have lately been stored in the memory area 76. The control device 56 may erase, from the memory area 76, the sets of proper BP data on a first-input-first-output basis, if the memory area 76 is filled with the data. The oldest set of proper BP data may, or may not, be erased.

While in the illustrated embodiment the list 108 shows the pulse-rate value PR, together with the BP values, date, and time, for each of the four sets of proper BP data stored in the four memory areas 78–84, it is possible that the list 108 may show one or more different sorts of physical information, such as mean blood pressure MAP, which is/are obtained when the BP values are obtained. In addition, the BP measuring apparatus 10 may further employ a device for measuring a degree of arterial sclerosis of a living person. In the latter case, the list 108 may show the measured degree of arterial sclerosis with the BP values, date, and time.

It is to be understood that the present invention may be embodied with other changes, modifications, and improvements which may occur to those skilled in the art without departing from the spirit and scope of the invention defined in the appended claims.

What is claimed is:

1. An apparatus for measuring a blood pressure value of a living subject, comprising:
    a blood pressure measuring device which measures, in each of a plurality of measuring operations, at least one blood pressure value of the subject including a systolic blood pressure value of the subject;
    a first storing means for storing a set of blood pressure data which represents said at least one blood pressure value measured in said each measuring operation of said blood pressure measuring device, and a date and a time when said each measuring operation is carried out by said blood pressure measuring device, so that said first storing means stores a plurality of sets of blood pressure data corresponding to said plurality of measuring operations;
    a second storing means for storing a first one of said sets of blood pressure data which belongs to a first predetermined number of successive sets of blood pressure data including an oldest set of blood pressure data which are stored in said first storing means;
    a third storing means for storing a second one of said sets of blood pressure data which belongs to a second predetermined number of successive sets of blood pressure data including a second latest set of blood pressure data which are stored in said first storing means;
    a fourth storing means for storing a third one of said sets of blood pressure data which represents at least one blood pressure value including a highest systolic blood pressure value of the respective systolic blood pressure values represented by said sets of blood pressure data except for said first and second sets of blood pressure data;
    a fifth storing means for storing a fourth one of said sets of blood pressure data which represents at least one blood pressure value including a lowest systolic blood pressure value of the respective systolic blood pressure values represented by said sets of blood pressure data except for said first and second sets of blood pressure data; and
    a recording device which records, on a recording medium, (a) a graphic representation comprising a plurality of first symbols each of which is indicative of the at least one blood pressure value represented by a corresponding one of said sets of blood pressure data, in an order of said measuring operations, (b) a list containing the at least one blood pressure value, date, and time represented by each of said first, second, third, and fourth sets of blood pressure data, and (c) a second symbol in association with each of the four first symbols corresponding to said first, second, third, and fourth sets of blood pressure data, in said graphic representation.

2. An apparatus according to claim 1, wherein said recording device comprises means for recording, on said recording medium, said graphic representation such that said first symbols are plotted at a regular interval of distance along an axis indicative of said order of said measuring operations.

3. An apparatus according to claim 1, wherein said second storing means comprises means for storing, as said first set of blood pressure data, one of said sets of blood pressure data which represents the oldest date and time of the respective dates and times represented by said sets of blood pressure data.

4. An apparatus according to claim 1, wherein said third storing means comprises means for storing, as said second set of blood pressure data, one of said sets of blood pressure data which represents the second latest date and time of the respective dates and times represented by said sets of blood pressure data.

5. An apparatus according to claim 1, further comprising a sixth storing means for storing a set of temporary blood pressure data which represents at least one temporary blood pressure value comprising at least one blood pressure value measured by said blood pressure measuring device in each of a plurality of measuring operations within a predetermined time duration, thereby storing a plurality of sets of temporary blood pressure data corresponding to said plurality of measuring operations within said time duration, wherein said first storing means comprises means for selecting one of said sets of temporary blood pressure data which represents at least one temporary blood pressure value including a lowest temporary systolic blood pressure value of the respective temporary systolic blood pressure values represented by said sets of temporary blood pressure data, and storing a set of proper blood pressure data representing at least one proper blood pressure value including said lowest temporary systolic blood pressure value.

6. An apparatus according to claim 1, further comprising a card reader which reads identification data recorded on a data card which is inserted in said card reader by the subject.

7. An apparatus according to claim 6, wherein said first storing means comprises means for storing said sets of blood pressure data on the data card being inserted in said card reader.

8. An apparatus according to claim 6, further comprising:
    a registering device which registers identification data identical with the identification data recorded on the data card; and
    judging means for judging whether the identification data read by said card reader from the data card inserted by the subject are identical with the identification data registered by the registering device.

9. An apparatus according to claim 8, wherein said first storing means comprises means for accumulatively storing said sets of blood pressure data in association with the registered identification data.

10. An apparatus according to claim 1, wherein said blood pressure measuring device comprises means for measuring, in said each measuring operation, at least a systolic and a diastolic blood pressure value of the subject.

11. An apparatus according to claim 1, wherein said blood pressure measuring device comprises an inflatable cuff which is adapted to be wound around a body portion of the subject.

12. An apparatus according to claim 1, wherein said second storing means comprises means for selecting said first set of blood pressure data from said sets of blood pressure data stored by said first storing device, and a memory which stores the selected first set of blood pressure data.

13. An apparatus according to claim 1, wherein said third storing means comprises means for selecting said second set of blood pressure data from said sets of blood pressure data stored by said first storing device, and a memory which stores the selected second set of blood pressure data.

14. An apparatus according to claim 1, wherein said fourth storing means comprises means for selecting said third set of blood pressure data from said sets of blood pressure data stored by said first storing device, and a memory which stores the selected third set of blood pressure data.

15. An apparatus according to claim 1, wherein said fifth storing means comprises means for selecting said fourth set of blood pressure data from said sets of blood pressure data stored by said first storing device, and a memory which stores the selected fourth set of blood pressure data.

16. An apparatus according to claim 1, further comprising a pulse-rate measuring device which measures a pulse-rate value of the subject in said each measuring operation of said blood pressure measuring device, and wherein said first storing device stores said set of blood pressure data representing the pulse-rate value measured by said pulse-rate measuring device in said each measuring operation of said blood pressure measuring device.

17. An apparatus according to claim 1, wherein said first storing means comprises a memory which accumulatively stores said sets of blood pressure data.

* * * * *